US012796938B2

(12) United States Patent
Rozental et al.

(10) Patent No.: US 12,796,938 B2
(45) Date of Patent: Nov. 17, 2026

(54) MINIATURE ULTRASOUND DETECTION SYSTEM

(71) Applicant: TECHNION RESEARCH & DEVELOPMENT FOUNDATION LIMITED, Haifa (IL)

(72) Inventors: Amir Rozental, Haifa (IL); Yoav Hazan, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 19/100,691

(22) PCT Filed: Aug. 2, 2023

(86) PCT No.: PCT/IL2023/050802

§ 371 (c)(1),
(2) Date: Feb. 3, 2025

(87) PCT Pub. No.: WO2024/028874

PCT Pub. Date: Feb. 8, 2024

(65) Prior Publication Data

US 2026/0041323 A1 Feb. 12, 2026

Related U.S. Application Data

(60) Provisional application No. 63/394,388, filed on Aug. 2, 2022.

(51) Int. Cl.
*A61B 5/00* (2006.01)

(52) U.S. Cl.
CPC ............ *A61B 5/0095* (2013.01); *A61B 5/489* (2013.01)

(58) Field of Classification Search
None
See application file for complete search history.

(56) References Cited

U.S. PATENT DOCUMENTS

| | | | |
|---|---|---|---|
| 8,531,527 | B2 | 9/2013 | Chang et al. |
| 9,949,717 | B2 | 4/2018 | Rozental et al. |

(Continued)

FOREIGN PATENT DOCUMENTS

| | | | | |
|---|---|---|---|---|
| JP | 2001350036 A | 12/2001 | | |
| JP | 2016194655 A | 11/2016 | | |
| WO | WO-2020039427 A1 * | 2/2020 | ............... | G01H 9/00 |

OTHER PUBLICATIONS

"Kim et al.," "Air-coupled ultrasound detection using capillary-based optical ring resonators," Scientific Reports 7: 109 pp. 1-11 (Year: 2017).*

(Continued)

*Primary Examiner* — Patricia J Park
(74) *Attorney, Agent, or Firm* — The Roy Gross Law Firm, LLC; Roy D. Gross

(57) ABSTRACT

An ultrasound (US) detection system is disclosed. The US system, comprising: a wideband laser source configured to emit a wideband laser beam; a wideband pulse laser generator; an array of optical resonators configured to be impinged by an acoustic wave, the array is in optical communication with the wideband pulse laser generator, such that laser pulses generated by the wideband pulse laser generator resonate in the array of optical resonators, and an array of photodetectors, each photodetector is in optical communication with at least one corresponding optical resonator and configured to detect a change in the intensity of at least one laser pulse in response to impingement by the acoustic wave.

18 Claims, 9 Drawing Sheets

(56) References Cited

U.S. PATENT DOCUMENTS

2003/0223672 A1 12/2003 Joyner et al.
2008/0095490 A1 4/2008 Ashkenazi et al.
2011/0125004 A1* 5/2011 Thumma .............. A61B 5/0059 600/407
2014/0114187 A1* 4/2014 Rozental .................. A61B 8/44 600/407
2014/0301706 A1 10/2014 Ballato et al.
2016/0004342 A1 1/2016 Kyung et al.
2020/0196874 A1* 6/2020 Rozental .................. A61B 8/00
2020/0319019 A1* 10/2020 Westerveld ............ G01H 9/004
2022/0079451 A1 3/2022 Kellnberger et al.
2023/0380813 A1* 11/2023 Zhu ...................... A61B 8/4477

OTHER PUBLICATIONS

Campopiano, S., Cutolo, A., Cusano, A., Giordano, M., Parente, G., Lanza, G., & Laudati, A. (2009). Underwater acoustic sensors based on fiber Bragg gratings. Sensors, 9(6), 4446-4454. doi: 10.3390/s90604446. Epub Jun. 5, 2009. PMID: 22408534; PMCID: PMC3291919.
Moccia, M., Pisco, M., Cutolo, A., Galdi, V., Bevilacqua, P., & Cusano, A. (2011). Opto-acoustic behavior of coated fiber Bragg gratings. Optics express, 19(20), 18842-18860. doi: 10.1364/OE.19.018842. PMID: 21996827.
Rosenthal, A., Omar, M., Estrada, H., Kellnberger, S., Razansky, D., & Ntziachristos, V. (2014). Embedded ultrasound sensor in a silicon-on-insulator photonic platform. Applied Physics Letters, 104(2), 021116. doi:10.1063/1.4860983.
B. Ouyang, M. Haverdings, R. Horsten, M. Kruidhof, P. Kat, and J. Caro, Integrated photonics interferometric interrogator for a ring-resonator ultrasound sensor, Opt. Express 27, 23408-23421 (2019). doi: 10.1364/OE.27.023408. PMID: 31510622.
S. Sethuraman, J. H. Amirian, S. H. Litovsky, R. W. Smalling, and S. Y. Emelianov, Spectroscopic intravascular photoacoustic imaging to differentiate atherosclerotic plaques, Opt. Express 16, 3362-3367 (2008). https://doi.org/10.1364/OE.16.003362.
K. Jansen, A. F. W. van der Steen, H. M. M. van Beusekom, J. W. Oosterhuis, and G. van Soest, Intravascular photoacoustic imaging of human coronary atherosclerosis, Opt. Lett. 36, 597-599 (2011). doi: 10.1364/OL.36.000597. PMID: 21368919.
Kellnberger, S., Rosenthal, A., Myklatun, A., Westmeyer, G. G., Sergiadis, G., & Ntziachristos, V. (2016). Magnetoacoustic Sensing of Magnetic Nanoparticles. Physical Review Letters, 116(10), 108103. https://doi.org/10.1103/PhysRevLett.116.108103.
Wissmeyer G, Pleitez MA, Rosenthal A, Ntziachristos V. Looking at sound: optoacoustics with all-optical ultrasound detection. Light Sci Appl. Aug. 15, 2018;7:53. doi: 10.1038/s41377-018-0036-7. PMID: 30839640; PMCID: PMC6107019.
Zhang, C., Chen, S.-L., Ling, T., & Guo, L. J. (2015). Review of Imprinted Polymer Microrings as Ultrasound Detectors: Design, Fabrication, and Characterization. IEEE Sensors Journal, 15(6), 3241-3248. doi:10.1109/jsen.2015.2421519.
CY. Chao, L. J. Guo, S. Ashkenazi and M. O'Donnell, Ultrasound detection using polymer microring resonators, (CLEO). Conference on Lasers and Electro-Optics, 2005., Baltimore, MD, USA, 2005, pp. 758-760 vol. 1, doi: 10.1109/CLEO.2005.201913.
Chen, S.-L. & Huang, S.C.-H & Ling, T. & Ashkenazi, S. & Guo, L. (2009). Polymer Microring Resonators for High-Sensitivity and Wideband Photoacoustic Imaging. IEEE transactions on ultrasonics, ferroelectrics, and frequency control. 56. 2482-91. 10.1109/TUFFC.2009.1335.
Govindan V, Ashkenazi S. Bragg waveguide ultrasound detectors. IEEE Trans Ultrason Ferroelectr Freq Control. Oct. 2012;59(10):2304-11. doi: 10.1109/TUFFC.2012.2455. PMID: 23143579.
Rosenthal, A., Kellnberger, S., Bozhko, D., Chekkoury, A., Omar, M., Razansky, D., & Ntziachristos, V. (2014). Sensitive interferometric detection of ultrasound for minimally invasive clinical imaging applications. Laser & Photonics Reviews, 8(3), 450-457. doi: 10.1002/lpor.201300204.
Leinders, S., Westerveld, W., Pozo, J. et al. A sensitive optical micro-machined ultrasound sensor (OMUS) based on a silicon photonic ring resonator on an acoustical membrane. Sci Rep 5, 14328 (2015). https://doi.org/10.1038/srep14328.
S. Tsesses, D. Aronovich, A. Grinberg, E. Hahamovich, and A. Rosenthal, Modeling the sensitivity dependence of silicon-photonics-based ultrasound detectors, Opt. Lett. 42, 5262-5265 (2017). doi: 10.1364/OL.42.005262. PMID: 29240188.
M. F. Hossain, H. P. Chan, and M. A. Uddin, Simultaneous measurement of thermo-optic and stress-optic coefficients of polymer thin films using prism coupler technique, Appl. Opt. 49, 403-408 (2010). doi: 10.1364/AO.49.000403. PMID: 20090804.
C. Chao, S. Ashkenazi, S. Huang, M. O'Donnell and L. Guo, High-Frequency Ultrasound Sensors Using polymer microring resonators, IEEE Transactions on Ultrasonics, Ferroelectrics, and Frequency Control, vol. 54, No. 5, pp. 957-965 (2007). doi: 10.1109/TUFFC2007.341.
Zhang, E., Laufer, J., & Beard, P. (2008). Backward-mode multiwavelength photoacoustic scanner using a planar Fabry-Perot polymer film ultrasound sensor for high-resolution three-dimensional imaging of biological tissues. Applied Optics, 47(4), 561. doi:10.1364/ao.47.000561.
De Brabander, G. N., Boyd, J. T., & Beheim, G. (1994). Integrated optical ring resonator with micromechanical diaphragms for pressure sensing. IEEE Photonics technology letters, 6(5), 671-673. doi: 10.1109/68.285575.
D. J. Lockwood and L. Pavesi (Eds.), Silicon photonics II: components and integration (vol. 2), Springer, 2011.
D.X. Xu, J. H. Schmid, G. T. Reed, G. Z. Mashanovich, D. J. Thomson, M. Nedeljkovic, X. Chen, D. Van Thourhout, S. Keyvaninia, and S. K. Selvaraja, Silicon Photonic Integration Platform—Have We Found the Sweet Spot?, IEEE J. Sel. Top. Quantum Electron., vol. 20, No. 4, 8100217, 2014. doi: 10.1109/JSTQE.2014.2299634.
J. M. Cannata, T. A. Ritter, Wo-Hsing Chen, R. H. Silverman and K. K. Shung, Design of efficient, broadband single-element (20-80 MHZ) ultrasonic transducers for medical imaging applications, in IEEE Transactions on Ultrasonics, Ferroelectrics, and Frequency Control, vol. 50, No. 11, pp. 1548-1557, Nov. 2003, doi: 10.1109/TUFFC.2003.1251138.
Kopp, C, Bernabé, S., Bakir, B.B., Fédéli, J., Orobtchouk, R., Schrank, F, Porte, H., Zimmermann, L., & Tekin, T. (2011). Silicon Photonic Circuits: On-CMOS Integration, Fiber Optical Coupling, and Packaging. IEEE Journal of Selected Topics in Quantum Electronics, 17, 498-509. doi: 10.1109/JSTQE.2010.2071855.
J. L. Rose, Ultrasonic guided waves in solid media, Cambridge University Press, 2014. doi: 10.1017/CBO9781107273610.
M. F. Hossain, H. P. Chan, A. Z. Kouzani, and M. O. Goni, "Generalized characteristics of photo-elastic birefringence in polymer strip waveguides," Opt. Mater. Express 5, 1030-1044 (2015) https://doi.org/10.1364/OME.5.001030.
R. Ravi Kumar, E. Hahamovich, S. Tsesses, Y. Hazan, A. Grinberg and A. Rosenthal, Enhanced Sensitivity of Silicon-Photonics-Based Ultrasound Detection via BCB Coating, in IEEE Photonics Journal, vol. 11, No. 3, pp. 1-11, Jun. 2019, Art No. 6601311, doi: 10.1109/JPHOT.2019.2908013.
Rosenthal, A., Razansky, D., & Ntziachristos, V. (2011). High-sensitivity compact ultrasonic detector based on a pi-phase-shifted fiber Bragg grating. Optics Letters, 36(10), 1833. https://doi.org/10.1364/ol.36.001833.
T. Erdogan, "Fiber grating spectra," in Journal of Lightwave Technology, vol. 15, No. 8, pp. 1277-1294, Aug. 1997, doi: 10.1109/50.618322.
E. I. Green, "The Story of Q," American Scientist 43, 584-594 (1955). Available online: [https://www.jstor.org/stable/27826701].
Y.u Liu, S. B. Lee, and S. S. Choi, Phase-Shifted Fiber Bragg Grating Transmission Filters Based on the Fabry-Perot Effect, J. Opt. Soc. Korea 2, 30-33 (1998). https://doi.org/10.3807/JOSK.1998.2.1.030.
Hazan, Y., Levi, A., Nagli, M et al. Silicon-photonics acoustic detector for optoacoustic micro-tomography. Nat Commun 13, 1488 (2022). https://doi.org/10.1038/s41467-022-29179-7.
Y. Hou, S. Ashkenazi, S.-w. Huang and M. O'Donnell, Improvements in optical generation of high-frequency ultrasound, in IEEE

(56) References Cited

OTHER PUBLICATIONS

Transactions on Ultrasonics, Ferroelectrics, and Frequency Control, vol. 54, No. 3, pp. 682-686, Mar. 2007, doi: 10.1109/TUFFC.2007.292.
Zhao T, Su L, Xia W. Optical Ultrasound Generation and Detection for Intravascular Imaging: A Review. J Healthc Eng. Apr. 30, 2018;2018:3182483. doi: 10.1155/2018/3182483. PMID: 29854358; PMCID: PMC5952521.
Westerveld, W.J., Mahmud-Ul-Hasan, M., Shnaiderman, R. et al. Sensitive, small, broadband and scalable optomechanical ultrasound sensor in silicon photonics. Nat. Photonics 15, 341-345 (2021). https://doi.org/10.1038/s41566-021-00776-0.
Shnaiderman R, Wissmeyer G, Ülgen O, Mustafa Q, Chmyrov A, Ntziachristos V. A submicrometre silicon-on-insulator resonator for ultrasound detection. Nature. Sep. 2020;585(7825):372-378. doi: 10.1038/s41586-020-2685-y. Epub Sep. 16, 2020. PMID: 32939068.
Y. Hazan and A. Rosenthal, Simultaneous multi-channel ultrasound detection via phase modulated pulse interferometry, Opt. Express 27, 28844-28854 (2019). doi: 10.1364/OE.27.028844. PMID: 31684629.
Xu, M., & Wang, L. V. (2005). Universal back-projection algorithm for photoacoustic computed tomography. Physical Review E, 71(1). https://doi.org/10.1103/physreve.71.016706.
X. Luís Deán-Ben and Daniel Razansky, Portable spherical array probe for volumetric real-time optoacoustic imaging at centimeter-scale depths, Opt. Express 21, 28062-28071 (2013). https://doi.org/10.1364/OE.21.028062.
Luís Deán-Ben, X., Razansky, D. Adding fifth dimension to optoacoustic imaging: volumetric time-resolved spectrally enriched tomography. Light Sci Appl 3, e137 (2014). https://doi.org/10.1038/lsa.2014.18.
Deán-Ben, X., Bay, E. & Razansky, D. Functional optoacoustic imaging of moving objects using microsecond-delay acquisition of multispectral three-dimensional tomographic data. Sci Rep 4, 5878 (2014). https://doi.org/10.1038/srep05878.
O. Volodarsky, Y. Hazan, M. Nagli, and A. Rosenthal, Burst-mode pulse interferometry for enabling low-noise multi-channel optical detection of ultrasound, Opt. Express, OE 30, 8959-8973 (2022). doi: 10.1364/OE.449630. PMID: 35299336.
Volodarsky O, Hazan Y, Rosenthal A. Ultrasound detection via low-noise pulse interferometry using a free-space Fabry-Pérot. Opt Express. Aug. 20, 2018;26(17):22405-22418. doi: 10.1364/OE.26.022405. PMID: 30130935.
Antelius M, Gylfason KB, Sohlström H. An apodized SOI waveguide-to-fiber surface grating coupler for single lithography silicon photonics. Opt Express. Feb. 14, 2011;19(4):3592-8. doi: 10.1364/OE.19.003592. PMID: 21369182.
Y. Hazan and A. Rosenthal, Passive-demodulation pulse interferometry for ultrasound detection with a high dynamic range, Opt. Lett. 43, 1039-1042 (2018). doi: 10.1364/OL.43.001039. PMID: 29489775.
L. Riobó, Y. Hazan, F. Veiras, M. Garea, P. Sorichetti, and A. Rosenthal, Noise reduction in resonator-based ultrasound sensors by using a CW laser and phase detection, Opt. Lett. 44, 2677-2680 (2019). https://doi.org/10.1364/OL.44.002677.
R. Moisseev, A. Rosenthal; All-optical platform for ultrasound transmission matrix measurements. APL Photonics Oct. 1, 2024; 9 (10): 100801. https://doi.org/10.1063/5.0199554.
Pham K, Noimark S, Huynh N, Zhang E, Kuklis F, Jaros J, Desjardins A, Cox B, Beard P. Broadband All-Optical Plane-Wave Ultrasound Imaging System Based on a Fabry-Perot Scanner. IEEE Trans Ultrason Ferroelectr Freq Control. Apr. 2021;68(4):1007-1016. doi: 10.1109/TUFFC.2020.3028749. Epub Mar. 26, 2021. PMID: 33035154.
Alles, E.J., Fook Sheung, N., Noimark, S et al. A reconfigurable all-optical ultrasound transducer array for 3D endoscopic imaging. Sci Rep 7, 1208 (2017). https://doi.org/10.1038/s41598-017-01375-2.
Nagli M, Koch J, Hazan Y, Levi A, Ternyak O, Overmeyer L, Rosenthal A. High-resolution silicon photonics focused ultrasound transducer with a sub-millimeter aperture. Opt Lett. May 15, 2023;48(10):2668-2671. doi: 10.1364/OL.486567. PMID: 37186736.
PCT International Search Report and Written Opinion for International Application No. PCT/IL2023/050802, mailed Oct. 26, 2023, 9pp.

* cited by examiner

Prior Art

MINIATURE ULTRASOUND DETECTION SYSTEM

CROSS-REFERENCE TO RELATED APPLICATIONS

This application is a National Phase of PCT Patent Application No. PCT/IL2023/050802 having International filing date of Aug. 2, 2023, which claims the benefit of priority of U.S. Provisional Application No. 63/394,388, titled "MINIATURE ULTRASOUND DETECTION SYSTEM", filed Aug. 2, 2022, the contents of which are all incorporated herein by reference in their entirety.

FIELD OF THE INVENTION

The present invention relates generally to ultrasound detection systems. More specifically, the present invention relates miniature ultrasound detection system.

BACKGROUND OF THE INVENTION

The field of medical ultrasound has been largely enabled by the technological development of multi-element transducers, capable of transmitting complex acoustic patterns and detecting the resulting echoes at multiple locations simultaneously. The most widespread technology for ultrasound transducers is based on piezoelectric materials and commonly involves arrays with typical dimensions of several centimeters that achieve typical resolutions between 0.1 and 1 mm, where further miniaturization and higher resolutions have been hindered by both manufacturing challenges and loss of sensitivity. Nonetheless, there is a need for the imaging capabilities of ultrasound also in millimeter and sub-millimeter devices that could provide feedback during minimally invasive procedures.

Significant miniaturization may be achieved by capacitive micromachined ultrasonic transducers (CMUTs), they too suffer from signal reduction upon miniaturization, limiting their use in applications such as optoacoustic tomography and high-frequency pulse-echo ultrasound, in which high sensitivity is essential.

One of the promising approaches for miniaturizing ultrasound transducers and increasing their resolution is the use of optical techniques to generate and detect acoustic waves. In particular, optical resonators have been demonstrated to achieve considerably higher sensitivities for a given area than those of piezoelectric transducers or CMUTs. Nonetheless, many of the resonator platforms become impractical when the sensing elements are miniaturized significantly beyond 100 μm, resulting in arrays with a typical size of 1 cm. Recently, element miniaturization to the scale of 10 μm and below has been demonstrated with several silicon-photonics platforms, potentially enabling the fabrication of 100s of detectors in a millimeter-scale device.

Conventionally, detection is performed by monitoring the minute ultrasound-induced perturbations of the resonator's central frequency by tuning continuous-wave (CW) laser to the resonance central frequency and monitoring the output, by detecting the phase shift of the central frequency following the application of US pressure wave. However, fabrication errors and temperature or pressure gradients on the device often lead to a disparity in the resonance frequency of the array elements, requiring a separate laser per channel, individually tuned to its respective frequency, to enable simultaneous detection. Such a parallel detection is illustrated in FIG. 1. Parallelization may be achieved with a single source if pulse lasers are used that are sufficiently wide to cover all the resonances in the array, but the complexity of demodulating the frequency-encoded acoustic signals at the resonator outputs has limited the scalability of that approach.

Accordingly, there is a need for a new ultrasound detector array of resonators and a novel concept for scalable signal readout that exploits the dependence of the resonator's Q-factor and peak transmission (e.g., an amplitude modulation), rather than its central frequency. This new technique for analyzing the response of the resonator to pressure wave is the pulse transmission amplitude monitoring (PTAM).

SUMMARY OF THE INVENTION

Some aspects of the invention may be directed to an ultrasound detection system, comprising: a wideband laser source configured to emit a wideband laser beam; a wideband pulse laser generator; an array of optical resonators configured to be impinged by an acoustic wave, the array is in optical communication with the wideband pulse laser generator, such that laser pulses generated by the wideband pulse laser generator resonate in the array of optical resonators, and an array of photodetectors, each photodetector is in optical communication with at least one corresponding optical resonator and configured to detect a change in the intensity of at least one laser pulse in response to impingement by the acoustic wave.

In some embodiments, the change in the intensity is proportional to a pressure applied by the acoustic wave. In some embodiments, detecting a change in the intensity comprises detecting a change in the optical power transmission. In some embodiments, the system further comprises an ultrasound transducer configured to produce acoustic waves.

In some embodiments, the optical resonators are silicon-based resonators and the wideband laser beam is emitted at 1460 nm to 1600 nm. In some embodiments, the optical resonators are Silicon-Nitride-based resonators and the wideband laser beam is emitted at 400 nm to 1600 nm. In some embodiments, the optical resonators are polymer-based resonators and the wideband laser beam is emitted at 400 nm to 1600 nm. In some embodiments, the optical resonators are glass-based resonators and the wideband laser beam is emitted at 650 nm to 800 nm.

In some embodiments, the photodetectors are selected from, photodiodes, Photo-multipliers, Quantum dot photoconductors, and Phototransistors. In some embodiments, the array of optical resonators is dimensioned to be included in an insertable unit configured to be inserted in a catheter. In some embodiments, each optical resonator is selected from a group consisting of: π phase-shifted Bragg grating (π-BG), Fabry-Perot cavity, and optical-ring resonator. In some embodiments, the system further comprises a first optical fiber for delivering the wideband laser pulses to the array of optical resonators and a second optical fiber configured to deliver the resonated laser pulses from the array of optical resonators to the array of photodetectors.

Some additional aspects of the invention are directed to a method of imaging a blood vessel, comprising;

(a) controlling a wideband pulse laser source to emit a wideband laser beam;
(b) receiving from an array of photodetectors a signal related to an intensity of at least one laser pulse resonating in an array of optical resonators being in optical connection to the wideband pulse laser source;

(c) detecting a change in the intensity of at least one laser pulse in response to impingement by an acoustic wave reflected from the blood vessel;

(d) at least one of: analyzing the detected change, and generating an ultrasound image of the blood vessel.

In some embodiments, the method further comprises controlling an ultrasound transducer to generate an acoustic wave directed towards the blood vessel. In some embodiments, the blood vessel is a deep-tissue blood vessel. In some embodiments, the deep-tissue blood vessel is imaged during a medical procedure.

In some embodiments, the change in the intensity is proportional to a pressure applied by the acoustic wave. In some embodiments, detecting a change in the intensity comprises detecting a change in the optical power transmission.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
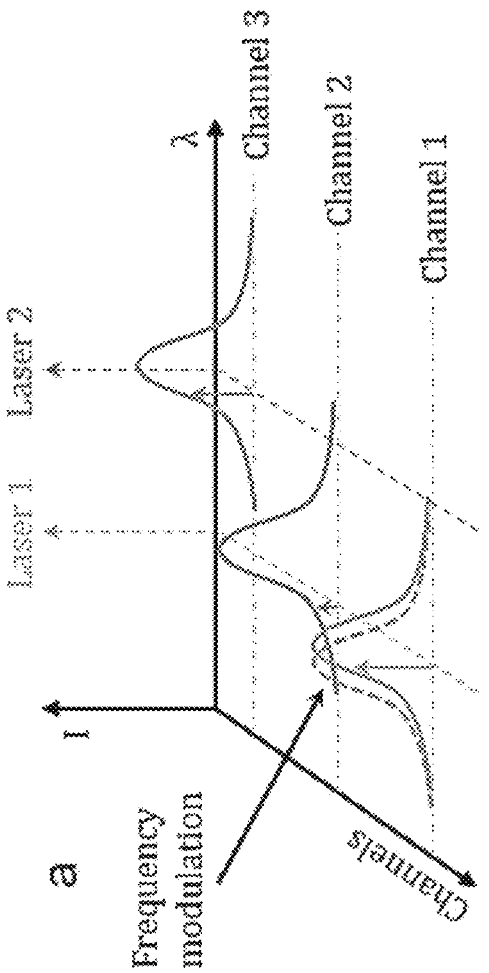
FIG. 1 includes graphs showing frequency modulation operation concept of conventional CW interrogation for detector array, requiring multiple lasers.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term "set" when used herein may include one or more items.

Unless explicitly stated, the method embodiments described herein are not constrained to a particular order or sequence. Additionally, some of the described method embodiments or elements thereof can occur or be performed simultaneously, at the same point in time, or concurrently.

Embodiments of the present invention disclose a method and an ultrasound detection system, that includes a wideband laser source emitting a single wideband pulsating laser beam and an array of optical resonators configured to be impinged by an acoustic wave. In some embodiments, the array of optical resonators may be miniaturized to be included in in vivo minimally invasive medical devices. Such a system may use a pulsating laser source in the input that covers the spectra of all the resonators in the array and a corresponding single photodetector at each output of each resonator to monitor the transmission amplitude of the resonator.

Figure 2A:
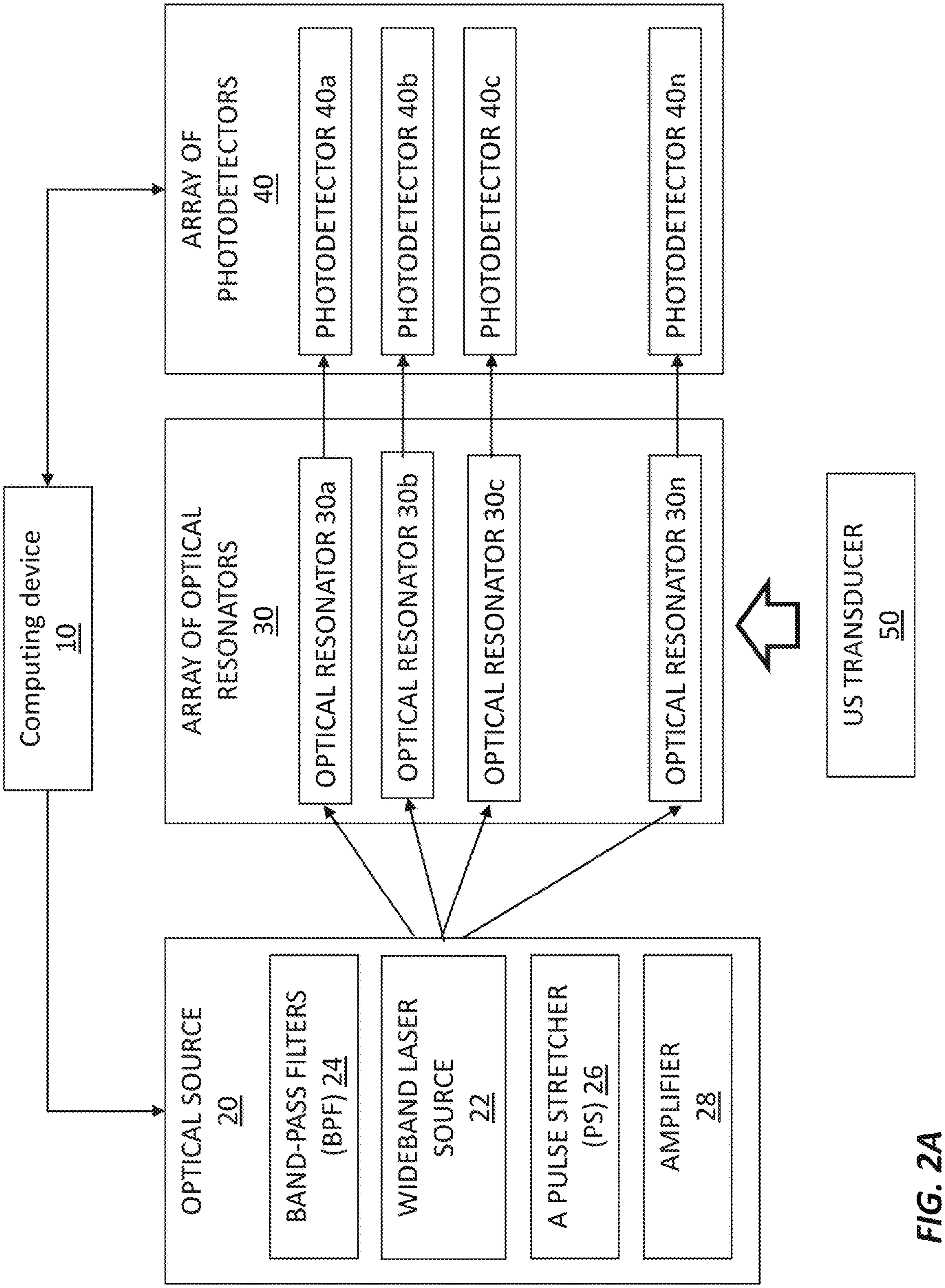
FIG. 2A depicting an ultrasound detection system according to some embodiments of the invention.
Figure 2B:
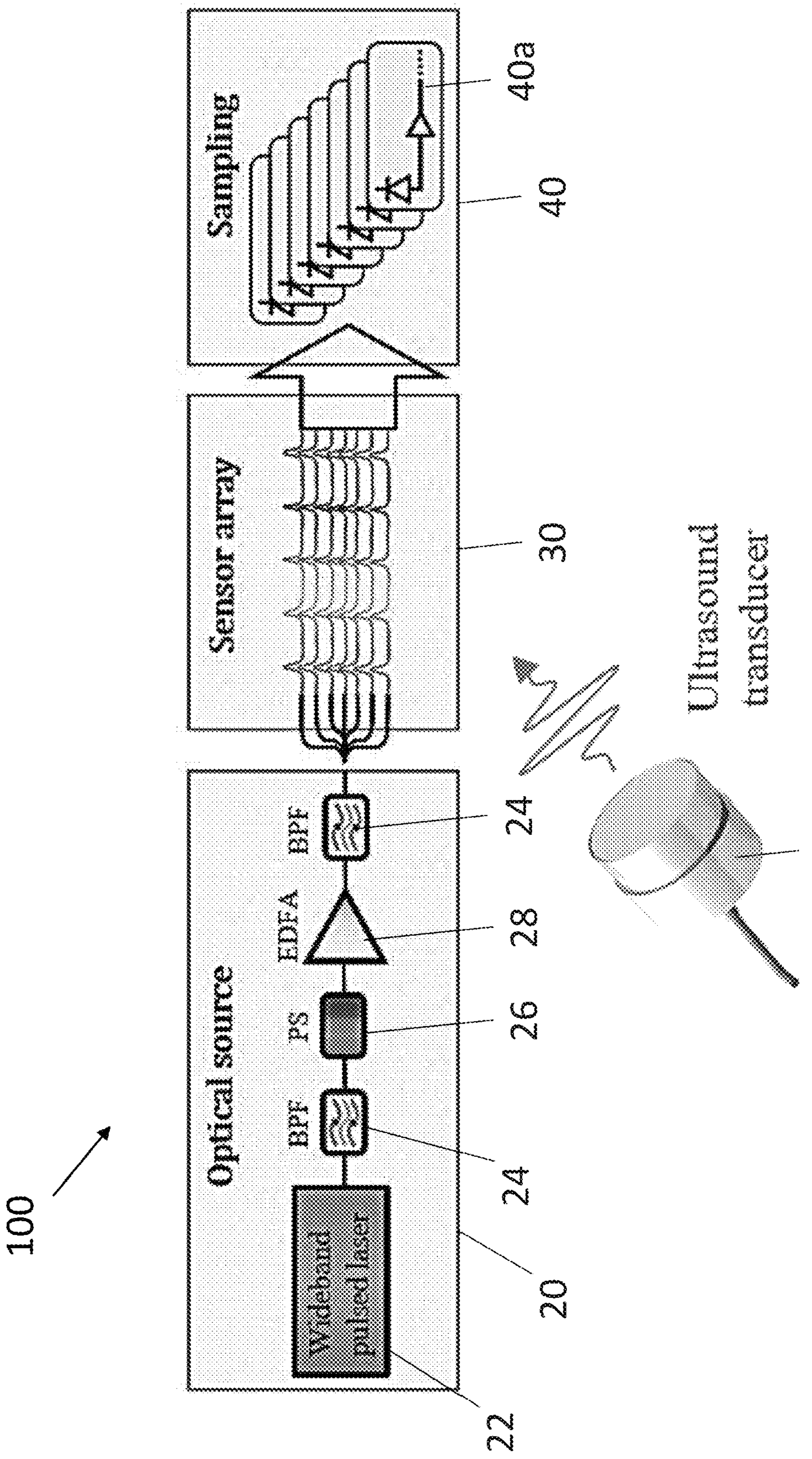
FIG. 2B is an illustration of a nonlimiting example for an ultrasound detection system according to some embodiments of the invention.

Reference is now made to FIGS. 2A and 2B which are block diagram and an illustration of an ultrasound detection system, according to some embodiments of the invention. A system 100 may include an optical source 20 comprising a wideband laser source 20 configured to generate a wideband laser beam. In some embodiments, optical source 20 may further include band-pass filters (BPF) 24, a pulse stretcher (PS) 26, and an amplifier 28 (e.g., Erbium-doped fiber amplifier (EDFA)). In some embodiments, the width of the laser band is selected according to the type of US resonators included in an array 30.

In some embodiments, system 100 may further include array 30 of optical resonators 30*a*-30*n* configured to be impinged by an acoustic wave. Array 30 is in optical communication with wideband pulse laser generator 22, such that laser pulses generated by wideband pulse laser generator 22 resonate in array 30 of optical resonators 30*a*-30*b*. In some embodiments, all resonators 30*a*-30*b* in array 30 are made from the same material, and may vary in the resonating wave due to differences in the manufacturing of each resonator. In some embodiments, optical resonators 30*a*-30*b* are silicon-based resonators and the wideband laser beam is emitted at 1460 nm to 1600 nm. In some embodiments, optical resonators 30*a*-30*n* are Silicon-Nitride-based resonators and the wideband laser beam is emitted at 400 nm to 1600 nm. In some embodiments, optical resonators 30*a*-30*b* are polymer-based resonators and the wideband laser beam is emitted at 400 nm to 1600 nm. In some embodiments, optical resonators 30*a*-30*n* are glass-based resonators and the wideband laser beam is emitted at 650 nm to 800 nm. In some embodiments, array 30 of optical resonators 30*a*-30*n* are dimensioned to be included in an insertable unit configured to be inserted in a catheter.

In the nonlimiting example, as illustrated in FIG. 2B array 30 includes 5×7 silicon-photonics π-phase shifted Bragg gratings (π-BG) resonators. However, as would be understood by one skilled in the art, the number of resonators n, according to embodiments of the invention, is equal to greater than 2. In some other nonlimiting examples, array 30 includes Fabry-Perot cavity resonators, optical-ring resonators and the like.

In some embodiments, system 100 may further include an array 40 of photodetectors 40*a*-40*n*, each photodetector is in optical communication with at least one corresponding optical resonator 30*a*-30*n*, include in a single channel, and configured to detect a change in the intensity of at least one laser pulse in response to impingement by the acoustic wave. In some embodiments, photodetectors 40*a*-40*n* are selected from, photodiodes, Photo-multipliers, Quantum dot photoconductors, Phototransistors and the like. In the nonlimiting example, of FIG. 2B each 5 silicon-photonics π-phase shifted Bragg gratings (π-BG) resonators in a single channel are in optical communication with a corresponding photodiode.

In some embodiments, the detected change in the intensity is proportional to a pressure applied by the acoustic wave, as discussed herein below. For example, detecting a change in the intensity comprises detecting a change in the optical power transmission.

In some embodiments, system 100 may further include a first optical fiber (not illustrated) for delivering the wideband laser pulses to array 30 of optical resonators and a second optical fiber (not illustrated) configured to deliver the resonated laser pulses from array 30 of optical resonators to array 40 of photodetectors.

In some embodiments, system 100 may further include an ultrasound transducer 50 configured to produce acoustic waves. In some embodiments, ultrasound transducer 50 may not be included in system 100 and may be an external device. In some embodiments, ultrasound transducer 50 may be any ultrasound transducer known in the art.

In some embodiments, system 100 may further include a computing device 10 configured to control at least laser source 22 to generate laser pulses and receive signals from array 40 of photodetectors. Computing device 10 may further be configured to analyze the received signals and to generate an US image, for example, the image illustrated in FIG. 8(*d*).

Figure 2C:
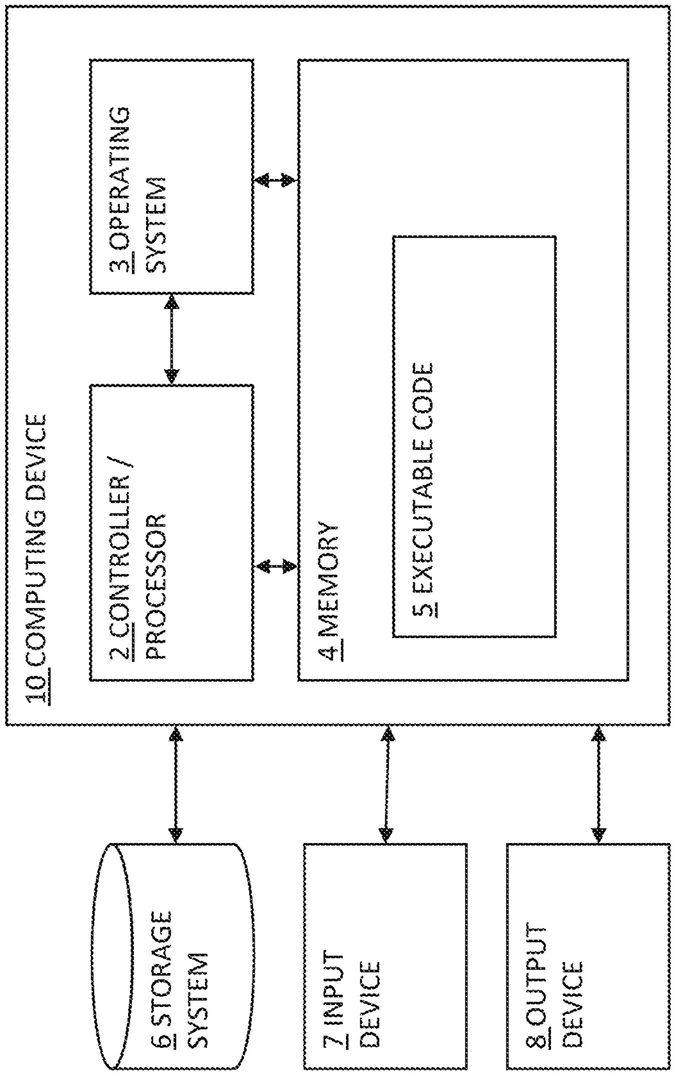
FIG. 2C is a block diagram, depicting a computing device which may be included in an ultrasound detection system according to some embodiments of the invention.

Reference is now made to FIG. 2C, which is a block diagram depicting a computing device, which may be included within an embodiment of an ultrasound detection system 100, according to some embodiments.

Computing device 10 may include a processor or controller 2 that may be, for example, a central processing unit (CPU) processor, a chip or any suitable computing or computational device, an operating system 3, a memory 4, executable code 5, a storage system 6, input devices 7 and output devices 8. Processor 2 (or one or more controllers or processors, possibly across multiple units or devices) may be configured to carry out methods described herein, and/or to execute or act as the various modules, units, etc. More than one computing device 10 may be included in, and one or more computing devices 10 may act as the components of, a system according to embodiments of the invention.

Operating system 3 may be or may include any code segment (e.g., one similar to executable code 5 described herein) designed and/or configured to perform tasks involving coordination, scheduling, arbitration, supervising, controlling or otherwise managing operation of computing device 10, for example, scheduling execution of software programs or tasks or enabling software programs or other modules or units to communicate. Operating system 3 may be a commercial operating system. It will be noted that an operating system 3 may be an optional component, e.g., in some embodiments, a system may include a computing device that does not require or include an operating system 3.

Memory 4 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 4 may be or may include a plurality of possibly different memory units. Memory 4 may be a computer or processor non-transitory readable medium, or a computer non-transitory storage medium, e.g., a RAM. In one embodiment, a non-transitory storage medium such as memory 4, a hard disk drive, another storage device, etc. may store instructions or code which when executed by a processor may cause the processor to carry out methods as described herein.

Executable code 5 may be any executable code, e.g., an application, a program, a process, task or script. Executable code 5 may be executed by processor or controller 2 possibly under control of operating system 3. For example, executable code 5 may be an application that may analyze signals received from array 40 in order to generate an US image, as further described herein. Although, for the sake of clarity, a single item of executable code 5 is shown in FIG. 2C, a system according to some embodiments of the invention may include a plurality of executable code segments similar to executable code 5 that may be loaded into memory 4 and cause processor 2 to carry out methods described herein.

Storage system 6 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) device or other suitable removable and/or fixed storage unit. Data may be stored in storage system 6 and may be loaded from storage system 6 into memory 4 where it may be processed by processor or controller 2. In some embodiments, some of the components shown in FIG. 2C may be omitted. For example, memory 4 may be a non-volatile memory having the storage capacity of storage system 6. Accordingly, although shown as a separate component, storage system 6 may be embedded or included in memory 4.

Input devices 7 may be or may include any suitable input devices, components or systems, e.g., a detachable keyboard or keypad, a mouse and the like. Output devices 8 may include one or more (possibly detachable) displays or monitors, speakers and/or any other suitable output devices. Any applicable input/output (I/O) devices may be connected to Computing device 10 as shown by blocks 7 and 8. For example, a wired or wireless network interface card (NIC), a universal serial bus (USB) device or external hard drive may be included in input devices 7 and/or output devices 8. It will be recognized that any suitable number of input devices 7 and output device 8 may be operatively connected to Computing device 10 as shown by blocks 7 and 8.

A system according to some embodiments of the invention may include components such as, but not limited to, a plurality of central processing units (CPU) or any other suitable multi-purpose or specific processors or controllers (e.g., similar to element 2), a plurality of input units, a plurality of output units, a plurality of memory units, and a plurality of storage units.

Figure 2D:
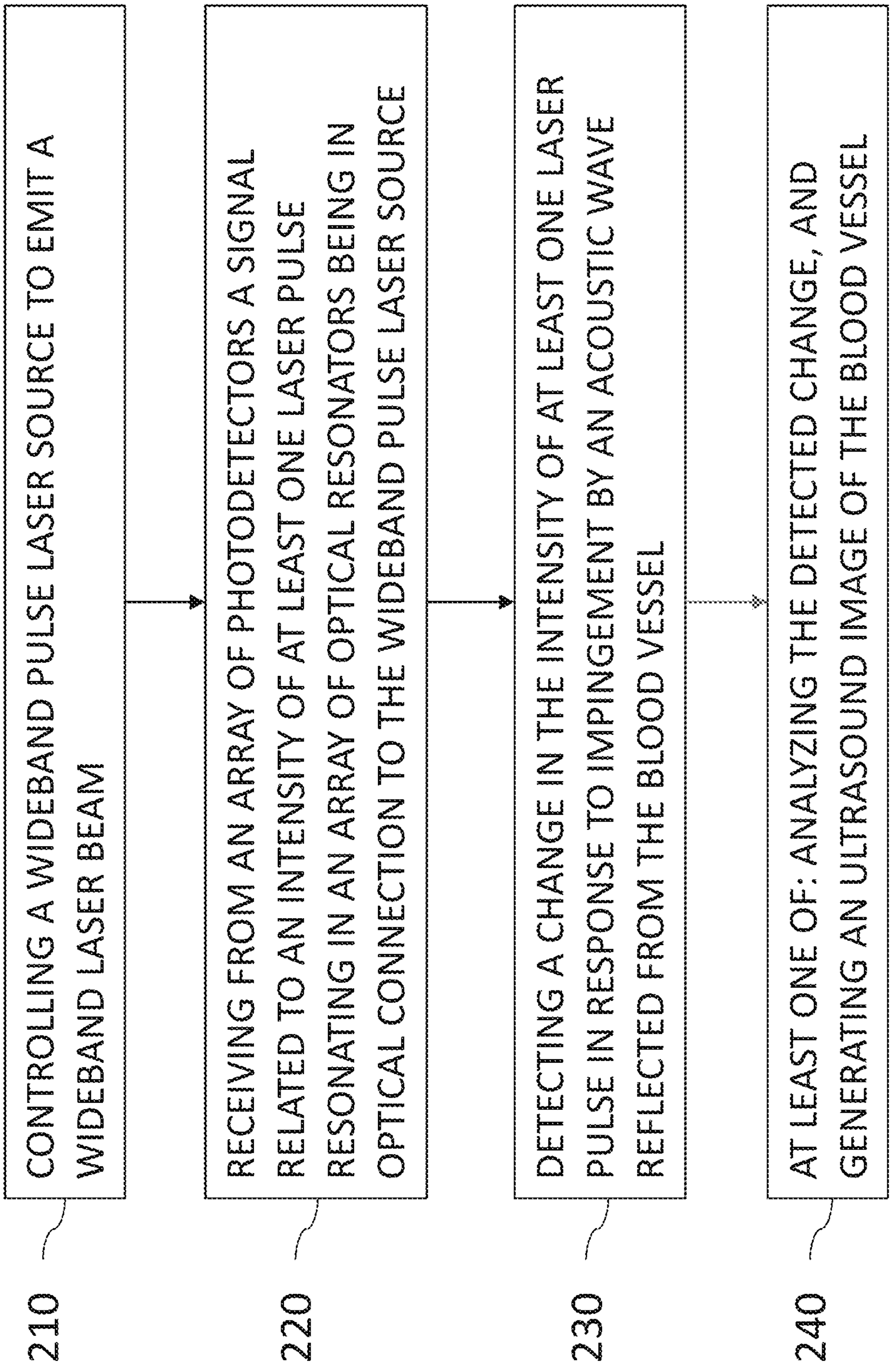
FIG. 2D is a flowchart of a method of imaging a blood vessel according to some embodiments of the invention.

Reference is now made to FIG. 2D which is a flowchart of a method of imaging a blood vessel according to some embodiments of the invention. In some embodiments, the blood vessel is a deep-tissue blood vessel, for example, imaged during a medical procedure. In some embodiments, the medical procedure may be selected from, a surgical procedure, stent implantation or any other medical intervention.

In some embodiments, computing device 10 may be configured to execute the following method steps:

Step 210—controlling wideband pulse laser source 22 to emit a wideband laser beam;

Step 220—receiving from array 40 of photodetectors a signal related to an intensity of at least one laser pulse resonating in array 30 of optical resonators being in optical connection to the wideband pulse laser source 22;

Step 230—detecting a change in the intensity of at least one laser pulse in response to an impingement by an acoustic wave, for example, reflected from the blood vessel; and Step 240—at least one of: analyzing the detected change and generating an ultrasound image of the blood vessel.

In some embodiments, the method may further include controlling ultrasound transducer 50 to generate an acoustic wave directed towards the blood vessel.

Comparison to CW Interrogation Technique

A comparison of the signal fidelity between PTAM and the most common interrogation technique of continuous wave laser interrogation (CW-I) was conducted. To demonstrate the high-fidelity signals acquired with PTAM compared to CW-I, the acoustic signals emitted from a 400 μm optoacoustic source positioned 1 mm away from the sensor, were measured, and scanned in the direction along the grating's length to acquire a one-dimensional sinogram using both techniques.

In CW-I, a CW laser is tunned slightly off the resonance frequency where the spectral transmission gradient is greatest, and thou frequency modulation translates into intensity modulation detected by a simple photodiode. Since the pressure perturbation modulating the resonance frequency occurs mainly at the location of the π-phase shift, the sensor preforms as a point detector. In PTAM, a wideband pulsed laser interrogates the resonator and the transmitted intensity is directly measured. The effect of the transmission amplitude modulation induced by pressure perturbation has to be localized at the resonator's position in order to yield a high-fidelity signal usable for imaging, similar to CW-I.

Figure 3:
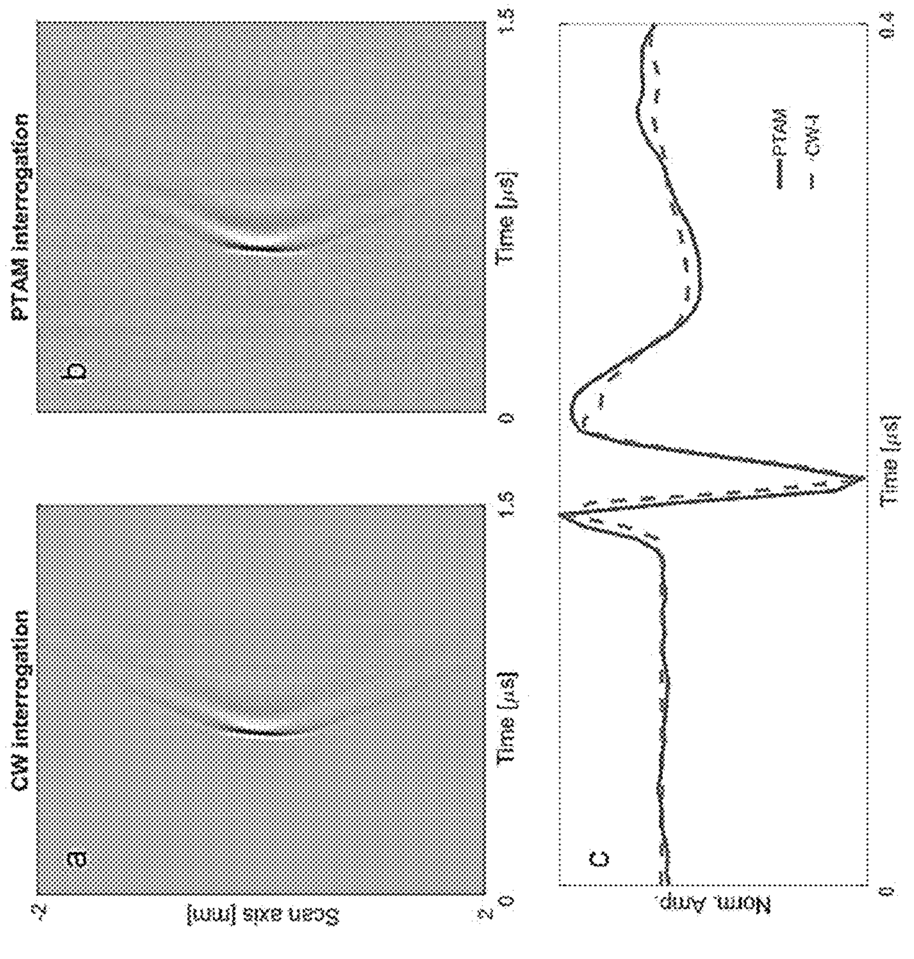
FIG. 3 includes sinogram and signal comparison of PTAM to CW interrogation technique according to some embodiment of the invention.

The measured signals and sinograms acquired with CW-I and PTAM, presented in FIG. 3. FIG. 3 shows a sinogram of 400 μm source measured with: (a) conventional CW interrogation technique and (b) PTAM interrogation technique. (c) Normalized acoustic signals for comparison PTAM with conventional CW (CW-I) interrogation technique. Nearly indistinguishable signals and sinograms are shown, confirming the amplitude modulation effect in PTAM is localized at the π-phase shift of the Bragg grating as well as in CW-I. This great signal integrity of PTAM compared to CW-I is crucial for imaging purposes. The only noticeable difference between PTAM and CW-I is the higher SNR achieved in CW-I. The SNR in PTAM may be increased by clever engineering of the sensor to increase the pressure induced losses.

Amplitude Modulation Analysis

Figure 4:
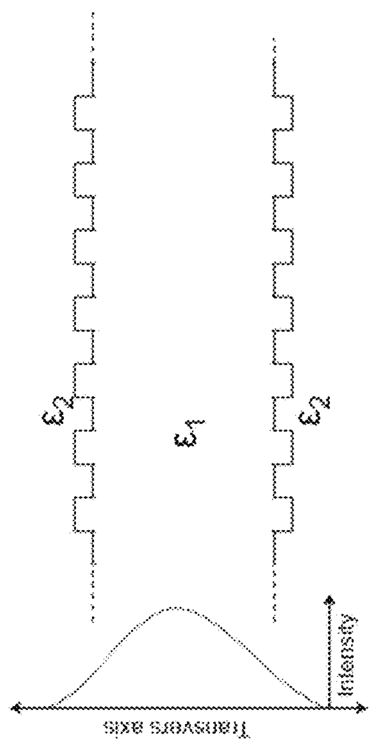
FIG. 4 are graphs showing Bragg grating structure of periodic width modulation according to some embodiments of the invention.

Reference is now made to FIG. 4, which include Bragg grating structure and Bragg grating structure of periodic width modulation. In some embodiments, the Bragg grating is formed by a periodic side corrugation of the width of a silicon waveguide, where the core permittivity is denoted by $\varepsilon_1$ and the elastomer-cladding permittivity by $\varepsilon_2$. The coupling coefficient of the grating is a product of the perturbation of the permittivity of the grating, due to it corrugation structure, and the modal cross-sections of the propagating and counter-propagation modes, as presented in equation (1)

$$\kappa(z) = \frac{\omega}{4}\int\int_{\infty} dxdy\Delta\varepsilon(x, y, z)\left|\vec{e}(x, y)\right|^2 \tag{1}$$

where $\Delta\varepsilon=\varepsilon_1-\varepsilon_2$ is the perturbation to the permittivity of the grating, and $\vec{e}$ is the optical mode cross-section. When the grating is used as an ultrasound detector, both ε1 and $\varepsilon_2$ are perturbed in proportion to the applied pressure modulation. If both the core and cladding had the same elasto-optic coefficient, the same permittivity change would occur in both ε1 and $\varepsilon_2$, leading to $\Delta\varepsilon=0$, and thus to a pressure-independent coupling coefficient κ. Nonetheless, in a such a device the effective refractive index would still vary in response to pressure, enabling the use of conventional interrogation techniques based on resonance-frequency monitoring. In our design, the elasto-optic coefficient of the PDMS cladding is significantly higher than that of the silicon core, and as a result Δε and κ become pressure dependent and can be modulated by acoustic waves.

The coupling coefficient κ determines the strength of the two Bragg reflectors, from each side of the π-phase jump, and thus the strength of the cavity. Specifically, the resonance bandwidth can be shown to be strongly depending on the coupling coefficient in the form of equation (2):

$$\Delta f = \frac{c}{2\pi} 4\kappa \exp(-\kappa L) \tag{2}$$

where c is the speed of light in the waveguide and L is the grating's length. The Q-factor is tied to the coupling coefficient by the resonance bandwidth, as the Q-factor is defined by equation (3):

$$Q \equiv \frac{f_{res}}{\Delta f} \tag{3}$$

In a non limiting example, this amplitude modulation effect is minute when the cladding is all silica, since the elasto-optic coefficients of silica are smaller than those of PDMS and are relatively close to those of silicon.

Although this analysis is accurate only for small coupling coefficients, it gives a qualitative explanation to the phenomenon of amplitude modulation, which depends on a strong asymmetry in the elasto-optic coefficient between the core and cladding. The inventors note that the pressure dependence of κ can lead to amplitude modulation via additional mechanisms, e.g. Bragg reflectors asymmetry limited by the fabrication yield, which may be amplified by perturbating ultrasound.

Methods and Examples

Figure 5:
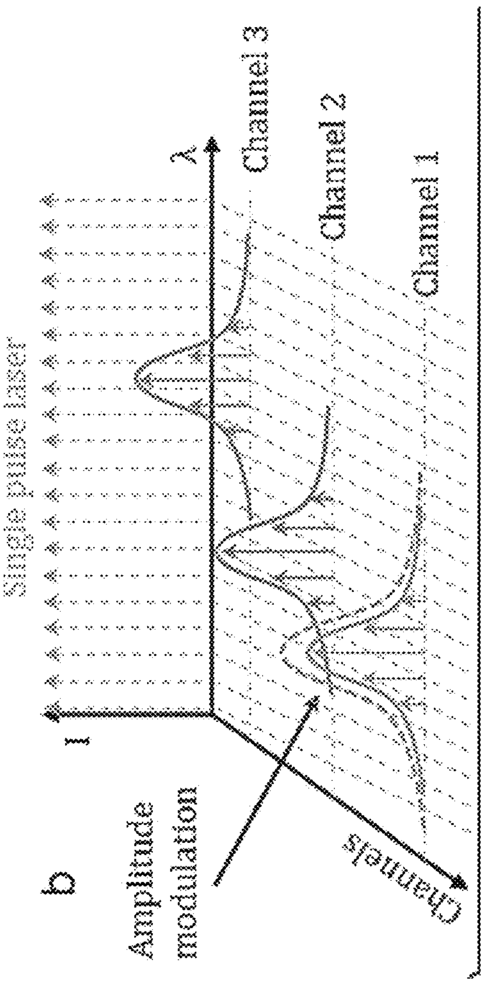
FIG. 5 includes of graphs showing an amplitude modulation PTAM generated using a single wideband laser beam according to some embodiments of the invention.

Reference is now made to FIG. 5, which shows graphs of amplitude modulation operation concept of PTAM for a detector array, according to some embodiments of the invention. The amplitude modulation showing a change in the amplitude intensity following an acoustic wave was conducted using the method disclosed herein above.

In a nonlimiting example, optical source 20 is composed of a femto-second laser with a bandwidth of 30 nm, which is filtered to a bandwidth of 1 nm using a tunable optical bandpass filter and subsequently amplified. The output of the source is split into 7 silicon-photonics waveguides, where in each waveguide 5 π-BG resonators were fabricated at different wavelength bands. In this specific example, the 7 waveguides were fabricated using the same design, most of the resulting resonances exhibited a poor spectral overlap, spanning a wavelength band of 0.7 nm in total. Therefore, a single CW laser is insufficient to simultaneously monitor the output of all the 7 resonators.

Figure 7:
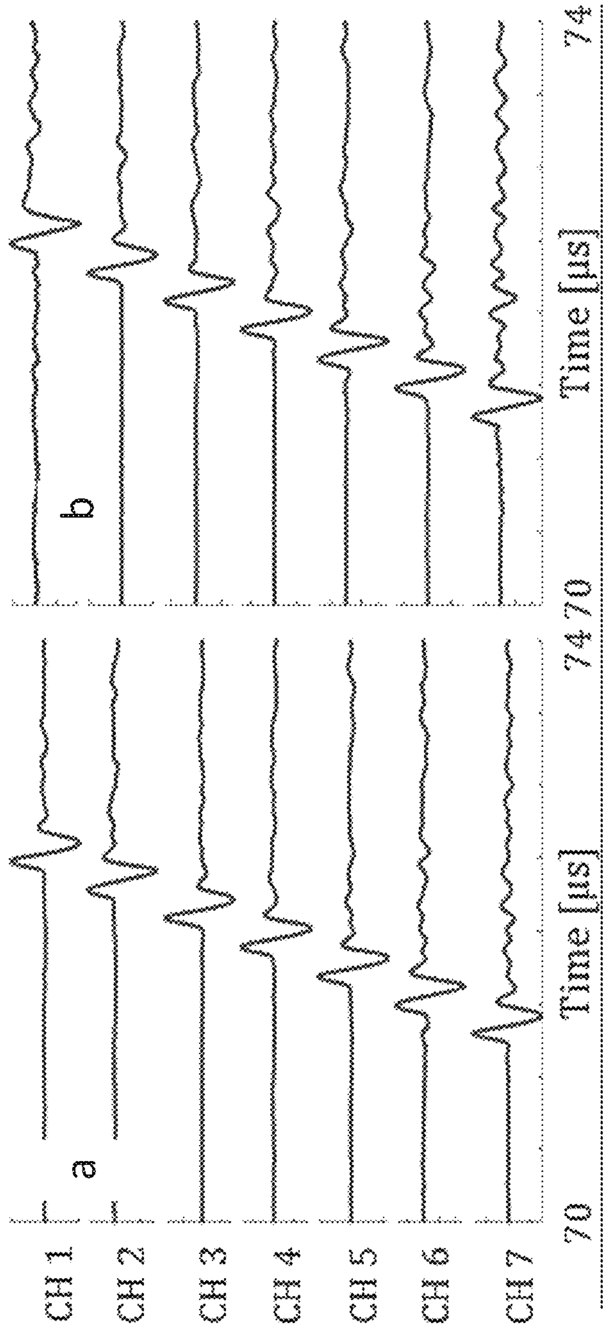
FIG. 7 includes graphs showing a slight delay difference of the ultrasound signal in response to a pressure wave along the detector array according to some embodiments of the invention.

The acoustic measurement setup included an ultrasound transducer with a central frequency of 5 MHz and a diameter of 25 mm (Olympus) positioned at a distance of approximately 110 mm from the silicon chip, where both the transducer and chip were submerged in water. An electronic pulser (PicoPulser, US Ultratek) delivered voltage bursts with a peak voltage of 300 V to the transducer to generate the acoustic pulses. The two optical bandpass filters were first tuned to the wavelength 1537.1 nm, in the center of Band 2, for the first measurement and to the wavelength 1561.5 nm, in the center of Band 3, for the second measurement. For each band, the acoustic signals were acquired with 64 averages to eliminate visible noise in the waveforms shown in FIGS. 7(*a*) and 7(*b*).

Figure 6:
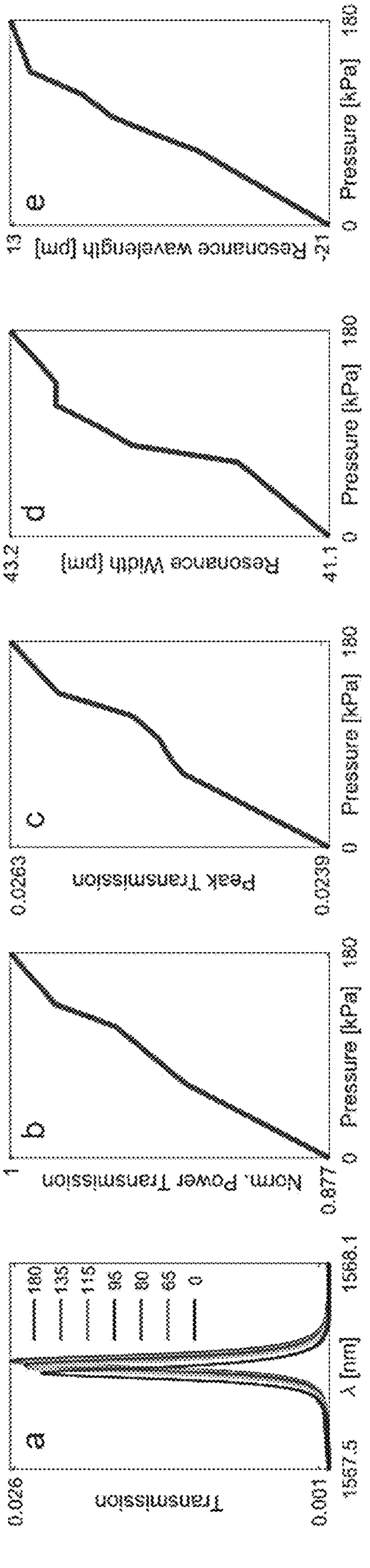
FIG. 6 includes graphs showing PTAM pressure measurements according to some embodiments of the invention.

Reference is now made to FIG. 6 which shows PTAM pressure measurements according to some embodiments of the invention. The effect of pressure on the transmission power of the resonance was tested for static pressure uniformly applied on array 30. FIG. 6(*a*) shows the transmission spectrum of a single π-BG at different pressure levels, where perturbations in both the central frequency and peak amplitude are readily observed. FIGS. 6(*b*)-(*e*) respectively shows the effect of pressure on the total transmission over the resonance bandwidth, which is the measured quantity in PTAM, the peak transmission, resonance bandwidth, and the effect on the central wavelength. As the figure shows, the increase in the total transmission of the resonance is a result of the combined increase in transmission peak and bandwidth.

The ability of PTAM for parallel acoustic detection was tested using an ultrasound transducer that produce acoustic burst that impinged on the silicon-photonics chip. The acoustic signals were first measured in parallel for the 7 channels in Band 2 and then the optical bandpass filters in the optical system (FIG. 1*c*) were adjusted to enable a measurement in Band 3; the measured acoustic signals are respectively shown in FIG. 7(*a*) and FIG. 7(*b*). To assess the compatibility of PTAM for high-fidelity acoustic sensing, the response was compared to an optoacoustic point source the response obtained with conventional CW interrogation technique, showing the compatibility of both methods, as discussed with respect in above in the Comparison to CW interrogation technique chapter. The measured sensitivity, expressed in the noise-equivalent pressure (NEP), in this measurement was 4.5 Pa/Hz-1/2 over an acoustic bandwidth of 60 MHz. While it has been shown that the acoustic bandwidth of π-BG resonators can exceed 200 MHz, the bandwidth limitation in this work is due to the multi-channel electronics used for parallel readout.

Figure 8:
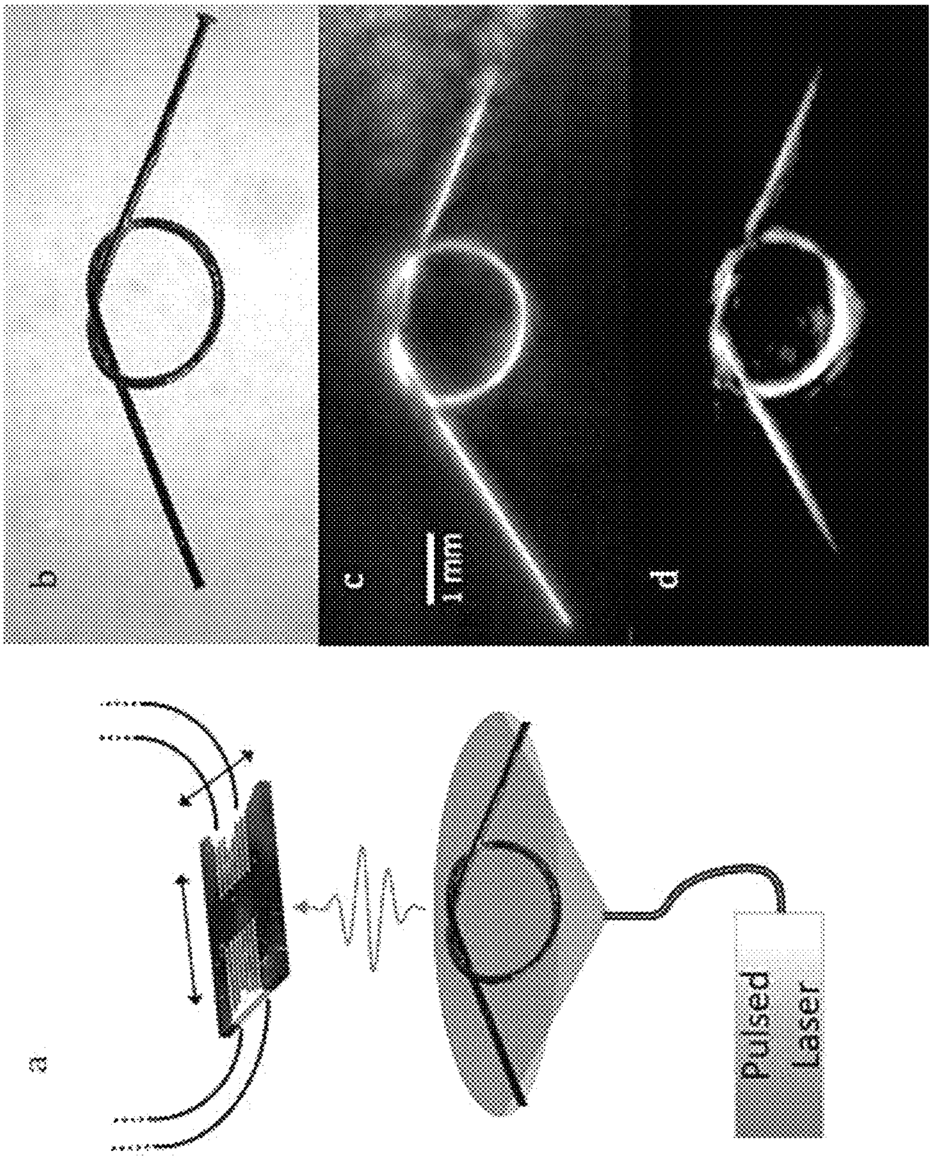
FIG. 8 includes images of a) a process of tomographic imaging using a system according some embodiments of the invention and (b) microscope image of suture tied into a knot. (c) Maximum intensity projection of optoacoustic image of the suture presented in (b), acquired using PTAM single channel from the array. (d) Maximum intensity projection of optoacoustic image of the suture presented in (b), acquired using PTAM array detection of 7 channels according to some embodiments of the invention.

Reference is now made to FIG. 8 which includes images of a) a process of tomographic imaging using a system according some embodiments of the invention and (b)-(d) images a 150 μm thick suture tied into a knot. FIG. 8(*b*) is a microscope image of the suture tied into a knot. The suture was tied to a knot and fixed in a solid agar medium to allow a clear aperture surrounding the suture. The suture was illuminated with optical laser pulses with a wavelength of 532 nm, pulse duration of 7 ns, and pulse energy of 30 mJ (INNOLAS, SpitLight EVO OPO). The suture and array 30 were submerged in water and the resonators 30*a*-30*g* were scanned over the suture with an overall span of 10 mm×10 mm and 100 μm step size.

The compatibility of PTAM with imaging applications was demonstrated in an optoacoustic-tomography measurement of a complex three-dimensional object, a 150 μm thick suture tied into a knot, illustrated in FIG. 8(*a*). The suture was embedded in an optically scattering medium and was illuminated with high-energy pulses, leading to a localized temperature increase and thermal expansion, which propagated outwards as an acoustic wave. The acoustic signals emanating from the suture were measured over a planar surface, resulting in three-dimensional tomographic data sufficient for reconstructing the structure of the imaged object. Two types of PTAM measurements were performed: in the first measurement, only a single resonator was used to read out the acoustic signals, requiring a full 2D scan of the silicon chip over the plane. In the second measurement, the 7 resonators in the array were read out in parallel and the step size of the scan in the corresponding direction was increased by a factor of 7 to avoid any spatial overlap between the detection positions of the array elements, leading to a 7-fold faster scan. In both types of measurements, the three-dimensional structure of the suture was reconstructed from the acoustic data using the universal back-projection algorithm. In the case of the 7-element array, the signals from each detector were normalized before the reconstruction to reduce the variability in the acoustic responsivity between the resonators. The maximum intensity projections of the three-dimensional reconstructions are shown in FIGS. 8(*c*) and 8(*d*) for the case of a single detector and 7-element array, respectively. The higher quality obtained in the single-element reconstruction may be explained by the lower signal variability achieved when a single resonator is used.

Closing Statement

A PTAM based system, according to embodiments of the invention, requires only a single pulse source, engineered to cover the wavelength span of the resonators, and a single photodetector per acoustic channel, making the technique scalable, potentially enabling simultaneous readout of hundreds of acoustic channels, as commonly performed with piezoelectric transducers. In contrast, parallel detection with the standard frequency-monitoring paradigm requires either high overlap between the resonator spectra, limiting the possible fabrication platforms, or complex setups in which expensive optical components need to be scaled up with the number of detection channels.

Unless explicitly stated, the method embodiments described herein are not constrained to a particular order or sequence. Furthermore, all formulas described herein are intended as examples only and other or different formulas may be used. Additionally, some of the described method embodiments or elements thereof may occur or be performed at the same point in time.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. An ultrasound detection system, comprising:

a wideband laser source configured to emit a wideband laser beam;

a wideband pulse laser generator;

an array of optical resonators configured to be impinged by an acoustic wave, the array is in optical communication with the wideband pulse laser generator, such that laser pulses generated by the wideband pulse laser generator resonate in the array of optical resonators; and an array of photodetectors, each photodetector is in optical communication with at least one corresponding optical resonator and configured to detect a change in an intensity of at least one laser pulse in response to impingement by the acoustic wave, wherein the change in the intensity is detected based on pulse transmission amplitude monitoring (PTAM), and wherein the change in intensity results from acoustic wave-induced modulation of the resonator's Q-factor and peak transmission.

2. The ultrasound detection system of claim 1, wherein the change in the intensity is proportional to a pressure applied by the acoustic wave.

3. The ultrasound detection system of claim 1, wherein detecting the change in the intensity comprises detecting a change in an optical power transmission.

4. The ultrasound detection system of claim 1, further comprising an ultrasound transducer configured to produce acoustic waves.

5. The ultrasound detection system of claim 1, wherein the optical resonators are silicon-based resonators, and the wideband laser beam is emitted at 1460 nm to 1600 nm.

6. The ultrasound detection system of claim 1, wherein the optical resonators are Silicon-Nitride-based resonators and the wideband laser beam is emitted at 400 nm to 1600 nm.

7. The ultrasound detection system of claim 1, wherein the optical resonators are polymer-based resonators and the wideband laser beam is emitted at 400 nm to 1600 nm.

8. The ultrasound detection system of claim 1, wherein the optical resonators are glass-based resonators and the wideband laser beam is emitted at 650 nm to 800 nm.

9. The ultrasound detection system of claim 1, wherein the photodetectors are selected from, photodiodes, Photo-multipliers, Quantum dot photoconductors, and Phototransistors.

10. The ultrasound detection system of claim 1, wherein the array of optical resonators is dimensioned to be included in an insertable unit configured to be inserted in a catheter.

11. The ultrasound detection system of claim 1, wherein each optical resonator is selected from a group consisting of: πphase-shifted Bragg grating (π-BG), Fabry-Perot cavity, and optical-ring resonator.

12. The ultrasound detection system of claim 9, further comprising a first optical fiber for delivering the laser pulses to the array of optical resonators and a second optical fiber configured to deliver the resonated laser pulses from the array of optical resonators to the array of photodetectors.

13. A method of imaging a blood vessel, comprising;

(a) controlling a wideband pulse laser source to emit a wideband laser beam;

(b) receiving from an array of photodetectors a signal related to an intensity of at least one laser pulse resonating in an array of optical resonators being in optical connection to the wideband pulse laser source;

(c) detecting a change in the intensity of at least one laser pulse in response to impingement by an acoustic wave reflected from the blood vessel, wherein the change in the intensity is detected based on pulse transmission amplitude monitoring (PTAM), and wherein the change in intensity results from acoustic wave-induced modulation of a Q-factor and peak transmission of the optical resonators; and (d) at least one of: analyzing the detected change and generating an ultrasound image of the blood vessel.

14. The method of claim 13, further comprising controlling an ultrasound transducer to generate an acoustic wave directed towards the blood vessel.

15. The method of claim 13, wherein the blood vessel is a deep-tissue blood vessel.

16. The method of claim 15, wherein the deep-tissue blood vessel is imaged during a medical procedure.

17. The method of claim 13, wherein the change in the intensity is proportional to a pressure applied by the acoustic wave.

18. The method of claim 13, wherein detecting the change in the intensity comprises detecting a change in an optical power transmission.

* * * * *